US00PP27117P3

(12) United States Plant Patent
Hansoti

(10) Patent No.: US PP27,117 P3
(45) Date of Patent: Aug. 30, 2016

(54) ***EPIPREMNUM* PLANT NAMED 'HANSOTI14'**

(50) Latin Name: *Epipremnum pinnatum*
Varietal Denomination: HANSOTI14

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 147 days.

(21) Appl. No.: 13/999,786

(22) Filed: Mar. 20, 2014

(65) Prior Publication Data

US 2015/0271976 P1 Sep. 24, 2015

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Cassandra Bright

(57) ABSTRACT

A new and distinct *Epipremnum* cultivar named 'HANSOTI14' is disclosed, characterized by compact growth habit, slow, controlled growth, distinctive green and yellow-green variegation. Leaves are medium sized, and broad ovate to broad deltate. The new variety is an *Epipremnum,* normally produced as an indoor potted plant.

2 Drawing Sheets

Figure 1:
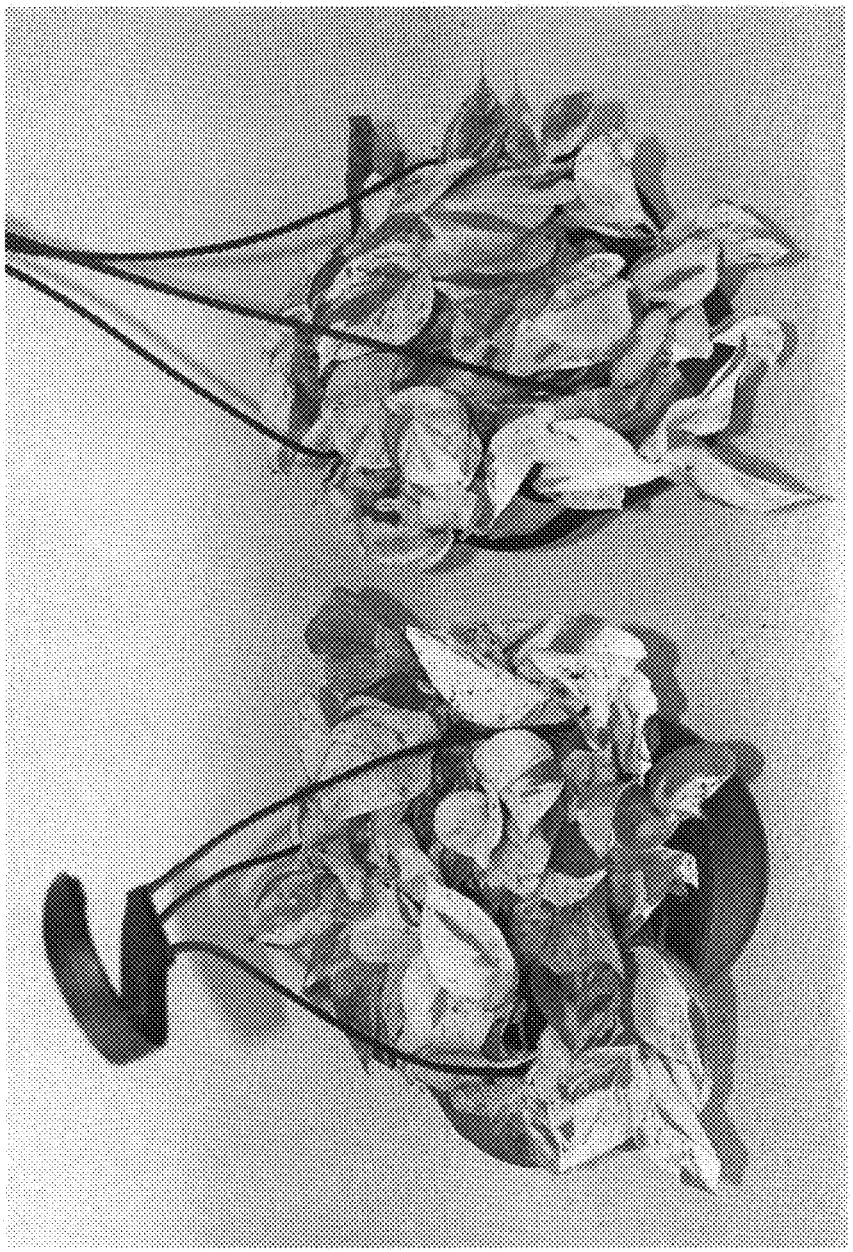

Latin name of the genus and species: *Epipremnum pinnatum.*

Variety denomination: 'HANSOTI14'.

BACKGROUND OF THE INVENTION

The new cultivar is a product of a planned breeding program. The object of the breeding program was to select and reproduce *Epipremnum pinnatum* plants with brighter variegation of the leaves, improved plant forms and interesting foliage shapes. The new variety was discovered as a naturally occurring branch mutation in a grouping of more than 1000 plants, representing superior clones of the parent variety, a proprietary selection of *Epipremnum pinnatum* 'Compacta'. Clones were selected for several years, with a selection criteria of shorter internodes and brightest variegation. The new variety was discovered by Ashish Arvind Hansoti in 2010 at a commercial greenhouse near Mumbai, India.

Asexual reproduction of the new cultivar 'HANSOTI14" by vegetative cuttings was performed at a commercial greenhouse outside of Mumbai, India and has shown that the unique features of this cultivar are stable and reproduced true to type on successive generations. Approximately 25 generations have been reproduced.

SUMMARY OF THE INVENTION

The cultivar 'HANSOTI14' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HANSOTI14'. These characteristics in combination distinguish 'HANSOTI14' as a new and distinct *Epipremnum'* cultivar:

1. Medium sized, broad ovate to broad deltate leaves.
2. Very compact growth with short internodes.

3. Bright, distinct marbled and blotched variegation pattern to the foliage.
4. Green and Yellow-Green variegation with both light and dark shades present on each leaf.
5. Strong petioles typically light Yellow-Green with a single Green stripe.
6. Early growth habit is mounding, then trailing with maturity.
7. Slow, controlled growth rate.

Plants of the new cultivar 'HANSOTI14' are similar to plants of the proprietary parent, *Epipremnum pinnatum* 'Compacta', unpatented, in most horticultural characteristics, however, plants of the new cultivar 'HANSOTI14' are shorter and produce much shorter internodes than the parent. Additionally, the new variety has a different leaf shape, with brighter variegation.

The new variety can be compared to the commercial variety, *Epipremnum pinnatum* 'NJOY', U.S. Plant Pat. No. 19,965. 'HANSOTI14' differs from 'NJOY' in the following characteristics:

1. Larger sized foliage.
2. Different shades of green of the foliage.
3. Different foliage shape.
4. Thicker petiole.
5. Different variegation pattern.

The new variety can be compared to the commercial variety, *Epipremnum pinnatum* 'Pearls and Jade', unpatented. 'HANSOTI14' differs from 'Pearls and Jade' in the following characteristics:

1. Larger sized foliage.
2. Different shades of green of the foliage.
3. Different foliage shape.
4. More mounding plant habit.
5. More variegation to the individual leaves.

BRIEF DESCRIPTION OF THE PHOTOGRAPHS

The accompanying photograph in FIG. 1 illustrates in full color two typical plants of 'HANSOTI14' grown in a polyhouse, in a 8 inch pot. Age of the plant photographed is approximately 24 weeks.

Figure 2:
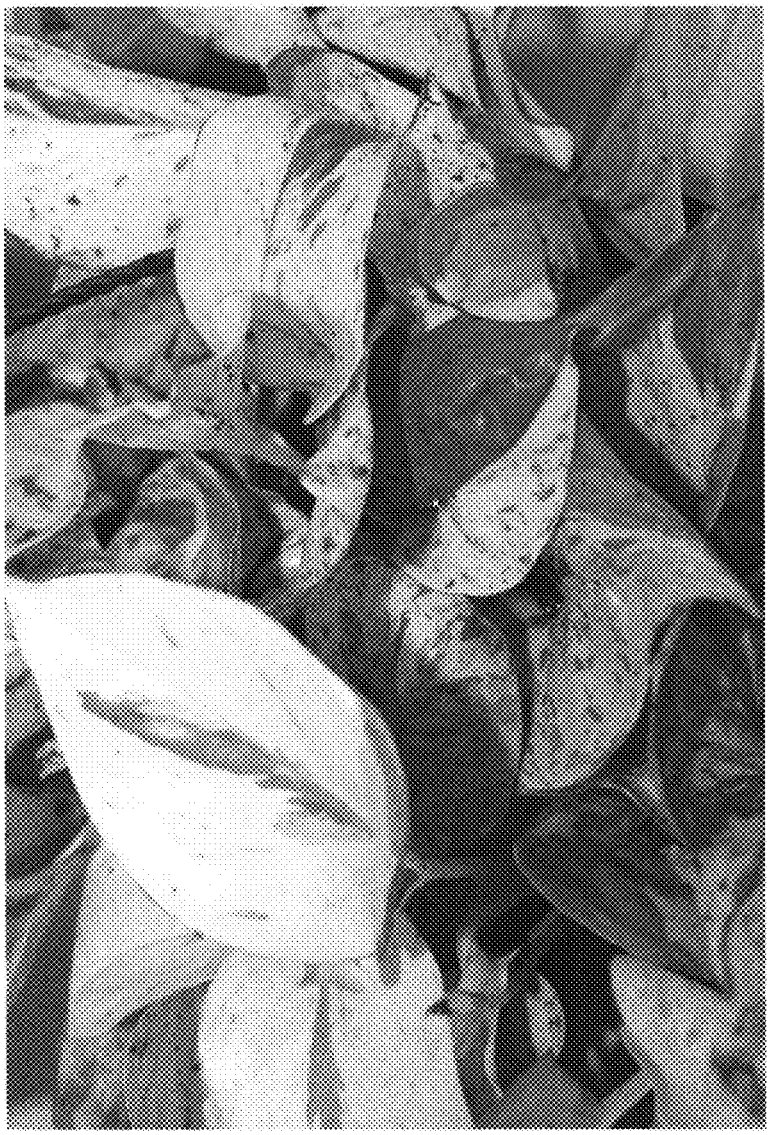

FIG. 2 illustrates in full color mature typical leaves of 'HANSOTI14' grown in a greenhouse, in Apopka, Fla.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HANSOTI14' plants grown in a poly plastic covered greenhouse in Apopka, Fla. The greenhouse is covered with an additional shade cloth, allowing 50% natural light through. The growing temperature ranged from approximately 10° C. to 20° C. at night and 20° C. to 35° C. during the day. Light levels were approximately 30-35 LUX. Measurements and numerical values represent averages of typical plant types.

Botanical classification: *Epipremnum pinnatum* 'HANSOTI14'.

PROPAGATION

Time to rooting: 20 days under summer conditions of approximately 25° C. to 40° C. 30 to 40 days under winter conditions of approximately 15° C. to ° 25° C.

Time to produce a rooted plant: Approximately 3 to 6 weeks.

Root description: Moderately fibrous. Aerial roots occasional seen under conditions of high humidity.

PLANT

Growth habit: Compact, Mounding then Semi-Trailing tender annual.

Height: Approximately 15 cm above a 8 cm pot.

Plant spread: Approximately 30 cm.

Growth rate: Slow.

Branching characteristics: Clusters of short new shoots are formed in the center of the plant, forming, trailing branches with age. Very free branching.

Length of lateral branches: Approximately 14 cm.

Number of leaves per lateral branch: Approximately 6 to 8.

Stem:

*Length*.—Approximately 12 to 15 cm.

*Diameter*.—Approximately 0.7 cm.

*Internode length*.—Average range 1.4 to 2.5 cm.

*Texture*.—Glabrous.

*Color*.—Near RHS 141B, streaks near Yellow-Green 145C.

Age of plant described: Approximately 22 weeks.

FOLIAGE

Leaf:

*Arrangement*.—Alternate.

*Average length*.—Approximately 8.5 (excluding petiole).

*Average width*.—Approximately 6.5 cm.

*Shape of blade*.—Broad ovate to broad deltate.

*Apex*.—Acuminate.

*Base*.—Subcordate.

*Attachment*.—Stalked.

*Margin*.—Entire.

*Aspect*.—Moderately undulating. Frequently upwardly folded.

*Texture of top surface*.—Smooth, slightly waxy.

*Texture of bottom surface*.—Somewhat leathery, smooth.

*Leaf internode length*.—Approximately 1 cm.

*Color*.—Young foliage upper side: Variegated, without a background coloration. All of the following colors are present: Darkest green on young foliage is Green 143A, present over approximately 10% of the leaf blade, occurring mainly along the margin, irregularly, not as a solid margin coloration pattern. Larger blotches, approximately 30% of leaf blade are Yellow-Green 144B. Approximately 30% of leaf blade is Yellow-Green 145C. Interior of the leaf blade, about 30% of the surface area, is closest to yellow-Green 150D. These colors occur either as individual blotches, or swirl together as a marbled effect. Young foliage under side: Under side of the Young Foliage is similar to the upper surface, however, has an overall less bright appearance: Variegated, without a background coloration. All of the following colors are present: Darkest green on young foliage is Green 143A, present over approximately 10% of the leaf blade, occurring mainly along the margin, irregularly, not as a solid margin coloration pattern. Larger blotches, approximately 30% of leaf blade are Yellow-Green 144B. Approximately 30% of leaf blade is Yellow-Green 145C. Interior of the leaf blade, about 30% of the surface area, is closest to yellow-Green 150D. These colors occur either as individual blotches, or swirl together as a marbled effect. Mature foliage upper side: Variegated, without a background coloration. Mainly a marbled effect, with some blotching of the darkest green. Darkest green on mature foliage is Green 137A, present over approximately 10% of the leaf blade, occurring as part of a marbled effect, or a blotch covering 10% to 20% of the leaf surface area. The marjority of the leaf surface area is marbled, Green 137C, Yellow-Green 144A, Yellow-Green 145C and 145D. Mature foliage under side: Underside of foliage tends to be less marbled than upper surface, and more blotchy. Large blotches of Yellow-Green 145C, 145D and Green 137A. Smaller blotches of Yellow-Green 144A.

*Venation*.—Type: Reticulate. Venation color upper side: Indistinguishable from foliage coloration. Venation color under side: Prominent mid-rib, typically colored yellow-Green 145D. Lateral veins indistinguishable from leaf blade coloration.

Petiole:

*Average length*.—Approximately 5.8 cm.

*Color*.—Near Yellow-Green 145C, with a streak of Green 137A.

*Diameter*.—Approximately 0.5 cm.

*Texture*.—Smooth.

*Strength*.—Strong.

FLOWER

Blooming not observed on the new cultivar.

OTHER CHARACTERISTICS

Disease resistance: Neither resistance nor susceptibility to diseases or pests has been observed in this variety.

Drought tolerance and cold tolerance: Tender annual. Tolerates low temperatures to 6° C. without damage. Tolerant of high humidity and temperatures to 40° C., with shade. No drought tolerance.

Fruit/seed production: Not observed.

What is claimed is:

1. A new and distinct cultivar of *Epipremnum* plant named 'HANSOTI14' as herein illustrated and described.

* * * * *